United States Patent [19]

Vehar

[11] Patent Number: 5,762,921
[45] Date of Patent: Jun. 9, 1998

[54] COMPOSITION AND METHODS FOR THE TREATMENT OF TUMORS

[75] Inventor: Gordon A. Vehar, San Carlos, Calif.

[73] Assignee: Genentech, Inc., South San Franciso, Calif.

[21] Appl. No.: 594,360

[22] Filed: Jan. 30, 1996

Related U.S. Application Data

[63] Continuation of Ser. No. 260,850, Jun. 16, 1994, abandoned.
[51] Int. Cl.$^6$ .......................... A61K 45/05; A61K 38/19; A61K 38/06; C07K 1/00
[52] U.S. Cl. .................. 424/85.1; 424/198.1; 424/85.2; 424/85.5; 424/158.1; 514/12; 530/350; 530/351; 530/381
[58] Field of Search ........................ 424/198.1, 85.2, 424/85.5, 85.1, 158.1; 514/12; 530/350, 351, 381

[56] References Cited

U.S. PATENT DOCUMENTS

| | | | |
|---|---|---|---|
| 4,506,009 | 3/1985 | Lenhoff et al. | 435/701 |
| 5,147,638 | 9/1992 | Esmon et al. | 424/145.1 |
| 5,196,404 | 3/1993 | Maraganore et al. | 514/3 |

FOREIGN PATENT DOCUMENTS

| | | |
|---|---|---|
| 0 589741 | 3/1994 | European Pat. Off. |
| 90/10081 | 7/1990 | WIPO |
| 91/01753 | 2/1991 | WIPO |

OTHER PUBLICATIONS

Bode and Stubbs, "Spatial Structure of Thrombin as a Guide to Its Multiple Sites of Interaction." *Seminars in Thromb. and Hemostasis* 19(4): 321–333 (1993).

Burrows and Thorpe, "Eradication of Large solid tumors in mice with an Immunotoxin Directed Against Tumor Vasculature," *Proc. Natl. Acad. Sci. USA 90:* 8996–9000 (1993).

Constantini and Zacharski, "Fibrin and Cancer," *Thromb. Haemost.* 69, 406–414 (1993).

de Fouw, N.J. et al., "The Interaction of Activated Protein C and Thrombin with the Plasminogen Activator Inhibitor Released from Human Endothelial Cells," *Thromb. Haemost.* 57(2), 176–182 (1987).

de Fouw, N.J. et al., *Fibrinogen, Thrombosis, Coagulation and Fibrinolysis.*, CY Liu and S. Chien, Eds. 235–243 (1990).

Esmon, C.T., "Protein S and Protein C, Biochemistry, Physiology, and Clinical Manifestation of Deficiencies," *Trends in Cardiovasc. Med.* 2, 214–219 (1992).

Esmon, N., "Thrombomodulin," *Prog. Hemost. Thr.* 9: 29–55 (1988).

Esmon, C., "The Roles of Protein C and Thrombomodulin in the Regulation of Blood Coagulation," *J. Biol. Chem.* 264, 4743–4746 (1989).

Glassman et al., "Thrombosis and Coagulation Abnormalities Associated with Cancer," *Ann. Clin. Lab. Sci.* 24, 1–5 (1994).

Ikeda and Stenflo, "A Radioimmunoassay for Protein C," *Thrombosis Res.* 39: 297–306 (1985).

Lehr, H. et al., *Am. J. Pathol.* 143: 1055–1062 (1993).

Leunig, M. et al., *Cancer Res.* 52: 6553–6560 (1992).

Miyamoto, S. et al., "Characterization of Heat-Treated Preparation of Human Protein C/Activated Protein C," *Thromb. Haemost.* 62: 920 (1989).

(List continued on next page.)

*Primary Examiner*—Lila Feisee
*Assistant Examiner*—Geetha P. Bansal
*Attorney, Agent, or Firm*—Ginger R. Dreger

[57] ABSTRACT

The invention concerns a method for inducing a selective collapse of the vasculature of a solid tumor by administering to a patient a therapeutically effective dose of a combination of a compound preventing the formation of a functional thrombin-thrombomodulin complex and a cytokine selected from the group of TNF-β (LT), TNF-α, IL-1, and IFN-γ. The invention further concerns the composition used in this method.

18 Claims, 2 Drawing Sheets

OTHER PUBLICATIONS

Nishioka, J. et al., "Estimation of the Possible Recongnition Sites for Thrombomdulin, Procoagulant, and Anti-coagulant Proteins around the Active Center of α-Thrombin," *J. Biochem. 114:* 148–155 (1993).

Nydahl, S. et al., "Thrombin Inactivation and the Effects of Antithrombin and Heparin in a Recirculating Langendorff Preparation,"*Thrombosis Res. 65,* 365–376 (1992).

Nydahl, S. et al., "Effect of Heparin on Thrombin Inhibition in the Microcirculation," *Thromb. Haemost. 69,* 41–44 (1993).

Palladino, M. et al., "Characterization of the Antitumor Activities of Human Tumor Necrosis Factor–α and the Comparison with other Cytokines: Induction of Tumor–Specific Immunity," *J. Immunol. 138:* 4023–4032 (1987).

Sakata, Y. et al., "Activated Protein C Stimulates the Fibrinolytic Activity of Cultured Endothelial Cells and Decreases Antiactivator Activity," *Proc. Natl. Acad. Sci. USA 82,* 1121–1125 (1985).

Sakata, Y. et al., "Mechanism of Protein C–Dependent Clot Lysis: Role of Plasminogen Activator Inhibitor," *Blood 68,* 1218–1223 (1986).

Scates, "Diagnosis and Treatment of Cancer–Related Thrombosis," *Sem. Thromb. Hemost. 18,* 373–379 (1992).

Suzuki, K. et al., "Localization of Thrombomodulin–binding Site within Human Thrombin," *J. Biol. Chem. 265* (22): 13263–13267 (1990).

Tanaka, S. et al., "Anti–Protein C Monoclonal Antibody Induces Thrombus In Mouse," *Thromb. Haemost. 62:* 377 (1989).

Taylor et al., "Protein C Prevents the Coagulopathic and Lethal Effects of *Escherichia Coli* Infusion in the Baboon," *J. Clin. Invest. 79,* 918–925 (1987).

Walker, F.J. and Fay, P.J., "Regulation of Blood Coagulation by the Protein C System," *FASEB J. 6,* 2561–2567 (1992).

Zacharski, "Basis for Selection of Anticoagulant Drugs for Therapeutic Trials in Human Malignancy," *Haemostasis 16,* 300–320 (1986).

Zacharski et al., "The Coagulation Biology of Cancer, " *Fibrinolysis 6,* 39–42 (1992).

Esmon, C.T., "The regulation of natural anticoagulant pathway" *Science* 235:1348–1352 (1987).

Jackman et al., "Characterization of a thrombomodulin cDNA reveals structural similarity to the low density lipoprotein receptor" *Proc. Natl. Acad. Sci. USA* 83:8834–8838 (1986).

Jackman et al., "Human thrombomodulin gene is intron depleted: nucleic acid sequences of the cDNA and gene predict protein structure and suggest sites of regulatory control" *Proc. Natl. Acad. Sci. USA* 84:6425–6429 (1987).

Kurosawa et al., "A 10–KDa cyanogen bromide fragment from the epidermal growth factor homology domain of rabbit thrombomodulin contains the primary thrombin binding site" *Journal of Biological Chemistry* 263:5993–5996 (1988).

Suzuki et al., "Structure and expression of human thrombomodulin, a thrombin receptor on endothelium acting as a cofactor for protein C activation" *EMBO Journal* 6:1891–1897 (1987).

Wen et al., "Human thrombomodulin: complete cDNA sequence and chromosome localization of the gene" *Biochemistry* 26:4350–4357 (1987).

Zacharski, "Basis for selection of anticoagulant drugs for therapeutic trials in human malignancy" *Haemostasis* 16:300–320 (1986).

Zacharski et al., "The coagulation biology of cancer" *Fibrinolysis* 6:39–42 (1992).

Zushi et al., "The last three consective epidermal growth factor–like structures of human thrombomodulin comprise the minimum functional domain for protein C–activating cofactor activity and anticoagulant activity" *Journal of Biological Chemistry* 264:10351–10353 (1989).

COMPOSITION AND METHODS FOR THE TREATMENT OF TUMORS

This is a continuation of application Ser. No. 08/260,850 filed on 16 Jun. 1994 (now abandoned), which application(s) is(are) incorporated herein by reference and to which application(s) priority is claimed under 35 USC § 120.

FIELD OF THE INVENTION

The present invention concerns compositions and methods for the treatment of tumors. More specifically, the invention concerns a method for inhibiting the growth and/or causing regression of microvasculated tumors by administering a combination of a procoagulant, such as a thrombomodulin inhibitor and a cytokine or an inducer of cytokine production.

BACKGROUND OF THE INVENTION

Thrombomodulin is a member of the protein C anticoagulant system (Walker, F. J. and Fay, P. J., FASEB J. 6, 2561–2567 [1992]; Esmon, C. T., Trends in Cardiovasc. Med. 2, 214–219 [1992]), which serves as the primary natural anticoagulant system of the capillary bed (Nydahl, S. et al., Thrombosis Res. 65, 365–376 [1992]; Nydahl, S. et al., Thromb. Haemost. 69, 41–44 [1993]). Known members of this system are the vitamin K dependent protein, protein C, which, when activated, is the central enzyme of this anticoagulation pathway, protein S (another vitamin K dependent protein), C4 binding protein, thrombomodulin, and thrombin. As illustrated in FIG. 1, these proteins react with other members in the system in a complex manner that leads to protein C activation Thrombomodulin, which is an integral membrane protein present on endothelial cells, is believed to function by binding thrombin to form a complex which catalyzes the activation of protein C. Physiologically, free thrombin has a number of procoagulant activities, including fibrin formation, platelet activation, and activation of factors V, VIII and XIII, but it is not able to activate protein C. Once thrombin is bound by thrombomodulin, it looses all of its procoagulant functions, and the thrombin/thrombomodulin complex now effectively catalyzes the activation of protein C at a specific Arg./Leu bond. The cleavage results in conformational changes that yield a functional serine protease. The activated protein C, in combination with protein S and a phospholipid surface, then catalyzes the proteolytic inactivation of coagulation factors V and VIII. Without factors V and VIII, the coagulation cascade cannot function and no fibrin will form. In addition to functioning as an anticoagulant, activated protein C may also promote fibrinolysis (de Fouw, N. J. et al., Fibrinogen, Thrombosis, Coagulation and Fibrinolysis., CY Liu and S. Chien, Eds. 235–243 [1990]). This action includes complex formation between activated protein C and plasminogen activator inhibitor 1 (PAI-1) (Sakata, Y. et a., Proc. Natl. Acad. Sci. USA 82, 1121–1125 [1985]; Sakata, Y. et al., Blood 68, 1218–1223 [1986]; de Fouw, N. J. et al., Thromb. Haemost. 57(2), 176–182 [1987]).

The important role of the protein C system, and protein C and thrombomodulin specifically, in the negative regulation of blood coagulation is well demonstrated, and it is known that any shift in the balance towards coagulation may produce serious pathological conditions with the potential of catastrophic consequences. Protein C deficiency has been correlated with increased risk of venous thrombosis and tissue necrosis. It has also been suggested that the failure to adequately activate protein C might contribute to the pathological injury in septic shock, and activated protein C has been proposed to be useful for the treatment of early stages of septic shock (Taylor et al., J. Clin. Invest. 79, 918–925 [1987]; Esmon J. Biol. Chem. 264, 4743–4746 [1989]; Esmon, C. T., Trends in Cardiovasc. Med. 2, 214–219 [1992]).

The relationship between blood coagulation and cancer gas highly controversial. Abnormalities of hemostasis in cancer patients have long been recognized. Thrombosis and hypercoagulability are reported in as many as 60% of patients with malignancies (Glassman et al., Ann. Clin. Lab. Sci. 24, 1–5 [1994]), while others noted that approximately 15% of patients with cancer will have a thrombotic event at some time (Scates, Sem. Thromb. Hemost. 18, 373–379 [1992]). Fibrin deposition was observed in a variety of solid tumors, such as small cell carcinoma of the lung (SCCL), renal cell carcinoma (RCC) and malignant melanoma (Constantini and Zacharski, Thromb. Haemosz. 69, 406–414 [1993]). Based upon the ability of antithrombotic (anticoagulant and antiplatelet) drugs to impede the progression of tumors in tumor-bearing experimental animals, it has been proposed that blood coagulation reactions contribute to the growth and spread of certain types of cancers (Zacharski, Haemostasis 16, 300–320 [1986]). Certain anticoagulants, such as warfarin and heparin were shown to have favorable effects on the course of progression of SCCL in human clinical trials (Zacharski et al., Fibrinolysis 6, 39–42 [1992] and the references cited therein).

In contrast with the reported benefits of certain anticoagulants in tumor therapy, C. T. Esmon and P. C. Comp (U.S. Pat. No. 5,147,638, issued 15 Sep. 1992 and PCT Application Publication No. WO 91/0153, published 21 Feb. 1991) described that certain inhibitors of the protein C anticoagulant system, either alone or fin combination with the administration of cytokines and/or other anti-tumor agents, have a marked inhibitory effect on tumor growth and, in many instances, result in dramatic tumor regression (U.S. Pat. No. 5,147,638 issued 15 Sep. 1992). The authors have found empirically that a protein C neutralizing antibody (HPC4) causes extensive clotting and subsequent necrosis within a wide variety of tumors, and that this effect is highly specific, leaving the normal tissue vasculature unaffected. The authors have specifically demonstrated that treatment of tumor-bearing animals with a protein C neutralizing antibody (HPC4) results in a dramatic reduction in tumor size, and that this effect is enhanced in some types of tumors by the coadministration of a cytokine, tumor necrosis factor (TNF).

SUMMARY OF THE INVENTION

The present invention is based on experiments demonstrating that the administration of lymphotoxin (LT, TNF-β) and inactivated thrombin in combination, but not inactivated thrombin or lymphotoxin alone, results in a total selective loss of blood flow to tumors in tumor-bearing animals. This, in turn, causes a substantially complete inhibition of tumor growth without any significant harm to normal tissue cells. As the inactivated (active-site blocked) exogenous thrombin is an inhibitor of the complex formation between active endogenous thrombin and thrombomodulin, protein C remains in its inactive, zymogenic form, i.e. the treatment is believed to result in a total blockage of the protein C system. In addition, the inactivated thrombin generates a more potent procoagulant stimulus than an antibody to protein C. With an antibody to protein C, any thrombin that is formed has its procoagulant activity neutralized upon binding to thrombomodulin in the vascular bed. When thrombomodulin is titrated out with inactivated thrombin, the microvasculature has lost both the ability to activate protein C as well as the ability to neutralize the procoagulant activities of thrombin through complex formation with thrombomodulin.

The present invention is additionally based on the experimental finding that a similar selective collapse of tumor vasculature and a resultant inhibition or tumor growth can be achieved by the administration of a combination of other agents that induce a procoagulant state and cytokines. Specifically, we have found that combinations of factor IXa and TNF-β, and tissue factor and TNF-β resulted in a total selective loss of blood flow to tumors in tumor-bearing animals.

In view of the extensive biomedical literature attesting to the benefits of anti-coagulant drugs in the treatment of malignancies it was entirely unforeseeable that compounds which evoke a procoagulant state, such as thrombomodulin-inhibitors, factor IXa and tissue factor, would be useful in tumor treatment. Furthermore, in view of the results reported by C. T. Esmon and P. C. Comp. supra, it is surprising that inactivated thrombin alone has no significant effect on the blood flow to tumors, whereas the administration of inactivated thrombin in combination with a cytokine (LT) results in a substantially complete occlusion of the capillaries growing into tumors within a few hours following administration, which, in turn, leads to dramatic tumor regression.

In one aspect, the present invention concerns a method for the treatment of a tumor in a patient comprising administering to the patient a therapeutically effective dose of a combination or a procoagulant and a cytokine or an inducer of cytokine production. The administration may be simultaneous or consecutive, with either the procoagulant or the cytokine or cytokine inducer being administered first. The patient preferably is human. In a preferred embodiment, the procoagulant is tissue factor or factor IXa or a combination thereof, while the cytokine is TNF-β, TNF-α, IL-1 and/or IFN-γ, most preferably TNF-β. The treatment may be combined with inhibition of one or more components of the protein C system and/or with other known tumor treatments.

In another aspect, the invention concerns a method for the treatment of a tumor in a patient comprising administering to the patient a therapeutically effective dose of a combination of a thrombomodulin inhibitor and a cytokine or an inducer of cytokine production. The administration may be simultaneous or consecutive, with either the thrombomodulin inhibitor or the cytokine or cytokine inducer being administered first. The patient preferably is human. In a preferred embodiment; the thrombomodulin inhibitor is an active-site blocked, altered (i.e. by amino acid substitution or insertion) or deleted thrombin molecule (which are collectively referred to as "inactivated thronbin"), most preferably a thrombin modified by site-specific mutagenesis at or around one or more of its active site residues, administered in combination with TNF-β (LT), TNF-α, IL-1 and/or IFN-γ. In an even more preferred embodiment, the cytokine is TNF-β. The treatment may be combined with inhibition of one or more further components of the protein C system and/or with other known tumor treatments.

In yet another aspect, the invention concerns a composition for the treatment of tumors in patients, comprising a therapeutically effective amount of a combination of a procoagulant and a cytokine or an inducer of cytokine production.

In a further aspect, the invention concerns a composition for the treatment of tumors in patients, comprising a therapeutically effective amount of a combination of a thrombomodulin inhibitor and a cytokine or an inducer of cytokine production.

In a further aspect, the invention concerns an antibody capable of specific binding to the thrombin-binding site(s) of thrombomodulin.

In yet another aspect, the invention concerns an antibody capable of specific binding to the thrombin/thrombomodulin complex, and is essentially unable to bind thrombin.

The invention further concerns hybridoma cell lines secreting the foregoing antibodies.

BRIEF DESCRIPTION OF THE DRAWINGS

FIGS. 2A–D are pictures taken prior to treatment (FIG. 2A) and at after treatment (FIGS. 2B–D) at the time points indicated.

DETAILED DESCRIPTION OF THE INVENTION

A. Definitions

Figure 1:
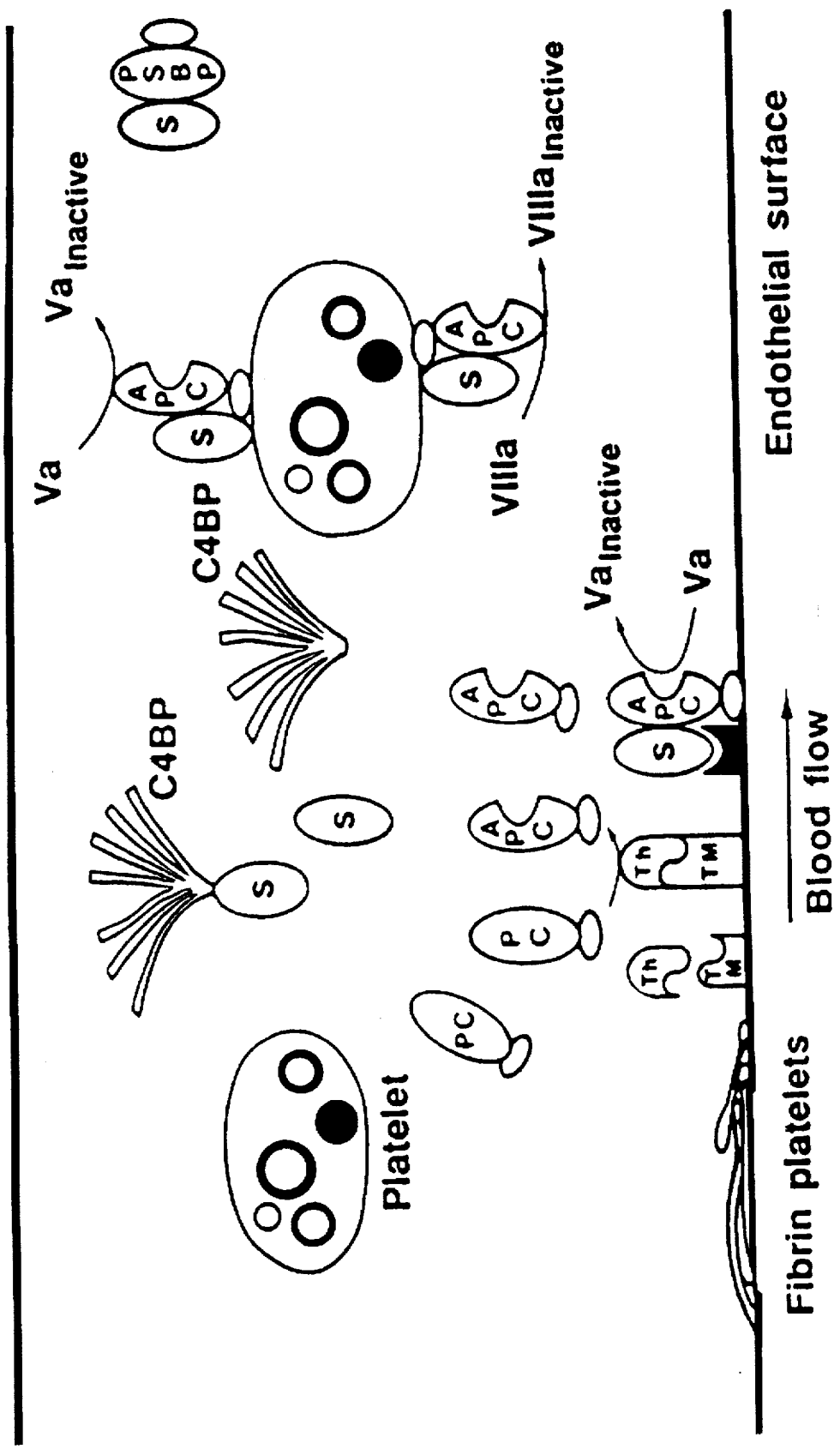
FIG. 1 (Esmon, C. T., Science 235, 1348–1352 [1987]) illustrates the known interactions among the members of the protein C anticoagulant pathway. The abbreviations used are as follows: PC: protein C; S: protein S; TM: thrombomodulin; Th: thrombin; APC: activated protein C; VIIIa: activated factor VIII; VIIIa$_{inactive}$: inactivated factor VIII; Va: activated factor V; Va$_{inactive}$: inactivated factor V; C4BP: C4 binding protein; PSBP: protein S binding protein.

The terms "tumor" and "cancer" are used interchangeably, and, along with their grammatical variants, refer to tumors of any cell type, including carcinomas, sarcomas, lymphomas and leukemias of any human and non-human animal species including swine, cats, dogs and higher primates. The methods and compositions of the present invention are particularly suitable for the treatment of solid tumors which are characterized by extensive vasculature (microvasculated tumors), including carcinomas, sarcomas and lymphomas of various cell types. Such tumors are surrounded by a fibrin capsule, and contain an extensive vasculature characterized by rapid proliferation of their endothelial cells, poor wall structure, increased permeability to plasma proteins, and a limited ability to increase blood flow in response to demand. Solid tumors particularly targeted by the treatment of the present invention include, but are not limited to, lung cancer; cancers of head and neck, including squamous cell and epidermoid carcinomas; adenocarcinomas, including prostatic, scirrhous, and mammary adenocarcinomas; lymphosarcoma; fibrosarcoma; leiomyosarcoma. chondroma; etc. The present method is particularly valuable in the therapy of disseminated solid tumors for which there are currently no effective treatments.

The term "procoagulant" is used herein to refer to any compound that has procoagulant activity or is capable of inducing a procoagulant state. The term specifically covers polypeptides, peptides and organic molecules, whether purified from native source, chemically synthesized or produced by techniques of recombinant DNA technology or by any combination of these and/or other methods, provided that they have the required procoagulant activity or ability to produce a procoagulant state. Such "procoagulants" include, but are by no means limited to, Factor IXa, tissue factor, factor VIIa, and factor XIa.

The term "thrombomodulin" is used to describe a native thrombomodulin expressed in any cell including endothelial cells of the micro- and macrocirculation) of any animal, eg., mammalian, species, including humans. The complete cDNA sequence and the amino acid sequence of native human thrombomodulin are known, as is the chromosome localization of the thrombomodulin gene (Dittman et al., Biochemistry 26, 4350–4357 [1987]; Jackman et al., Proc. Natl. Acad. Sci. USA 84, 6425–6429 [1987]; Suzuki et al.; EMBO J. 6, 1891–1897 [1987]). The human thrombomodulin cDNA encodes a protein of approximately 575 amino acids, composed of a highly hydrophobic, cysteine-poor and tryptophane-rich domain at the N-terminus, followed by a domain with six EGF-like repeats, a serine- and threonine-rich segment probably glycosylated through O-linkages, a transmembrane domain of about 23 hydrophobic amino acids and a cytoplasmic tail of about 38 amino acids (Esmon, N. L., Proc. Haemost. Thromb. 9, 29–58 [1988])

The terms "thrombin" and "α-thrombin" are used to describe an enzymatically active thrombin molecule that may, for example, result from cleavage of a native prochrombin expressed in any cell of any animal, e.g. mammalian, species, including humans, or made be made by methods of recombinant DNA technology, chemical synthesis, or any combination of these and/or other methods. The sequence, crystal structure, functions and interaction sites of native-sequence thrombins are well known in the art, and are, for example, disclosed in Bode, W. and Stubbs, M. T., Thromb. Haemost. 19, 321–333 (1993) and in the references cited therein.

The phrase "thrombomodulin inhibitor" as used herein refers to any compound or intervention that prevents the formation of a functional thrombin/thrombomodulin complex or that specifically recognizes and blocks the thrombin/thrombomodulin complex thereby preventing the activation of protein C. In the context of this definition, a "functional thrombin/thrombomodulin complex" is a complex formed in vivo between native thrombin and native thrombomodulin characterized by the ability of activating protein C.

The formation of a functional thrombin/thrornbomodulin complex can be prevented by one or more of the following approaches: (i) inhibiting the in vivo expression of thrombomodulin; (ii) selectively blocking thrombomodulin from binding thrombin; (iii) selectively blocking thrombin from binding thrombomodulin, and (iv) selectively blocking the thrombin/thrombomodulin complex, provided that if approach (i) is adapted, it should always be combined with at least one of methods (ii)–(iv).

The in vivo expression of thrombomodulin can, for example, be inhibited by IL-1, TNF-α, TNF-β and thrombin, which are known to downregulate thrombomodulin production and expression. Thrombomodulin expression on endothelial cells in a tumor may also be downregulated as a result of radiation treatment. X-irradiation in approximate doses of 100–300 rads delivered to the tumor bed is sufficient to cause mild local inflammation in the tumor, which is expected to lead to a loss of thrombomodulin expression.

Thrombomodulin can be selectively blocked by a neutralizing antibody or by any other compound (including organic molecules, peptides and polypeptides) capable of selective binding to the thrombin-binding site(s) of thrombomodulin. The major thrombin-binding domain of thrombomodulin has been localized on the 5th and/or 6th EGF-like repeats of the molecule (Kurosawa et al., *J. Biol. Chem.* 263, 5993–5996 [1988]; Zushi et al., *J. Biol. Chem.* 264, 10351–10353 [1989]); however, the first N-terminal domain of the molecule may also contribute to thrombin binding, either by stabilizing the EGF-like region or, alrernatively, by contributing to the proper conformation or the thrombin-binding site (Esmon, N. L. supra; Jackman et al., *Proc. Nat. Acad. Sci. USA* 83, 8834–8838 [1986]; Wen et al., *Biochemistry* 26, 4350–4357 [1987]). A facile way of blocking thrombomodulin is reaction with an active-site modified, deleted or blocked thrombin (inactivated thrombin) that retains its ability to bind to native thrombomodulin. This inactive form of thrombin binds to thrombomodulin but the complex formed is not capable of activating protein C. In this manner, with prior dosing of the inactivated thrombin, once functional thrombin is formed in the vasculature, all of the thrombomodulin will have been titrated out with the inactive form.

Thrombin can be selectively blocked by a neutralizing antibody or other compound (e.g. organic molecule, peptide or polypeptide) capable of inhibiting the thrombin/thrombomodulin interaction; e.g. by selective binding to the thrombomodulin-binding site(s) of thrombin, without inactivating thrombin. The region involved in binding of thrombomodulin (as well as fibrinogen, thrombin receptor, fibrin, and hirudin) has been found within the "fibrinogen recognition exosite" marked by "F" in FIG. 2 of Bode and Stubbs, supra. The unique property of thrombin to use the same or overlapping binding regions for various members of the coagulation cascade explains how the thrombin specificity is changed from procoagulant to anticoagulant. Thrombomodulin binds over the site that is used by thrombin to recognize its substrates; and aids in the generation of a site for protein C binding. Accordingly, thrombin can be selectively blocked by neutralizing the site required for thrombomodulin binding without neutralizing the site required for substrate recognition. Peptides that specifically inhibit the interaction of thrombin with thrombomodulin have been disclosed by Suzuki et al., *J. Biol. Chem.* 265, 13263–13267 [1990]; Suzuki & Nishioka, *J. Biol. Chem.* 266, 18498–18501 [1991] and Nishioka et al., *J. Biochem* 114, 148–155 [1993].

An alternative method of thrombomodulin inhibition is based on the different binding specificities of the thrombin/thrombomodulin complex and free thrombin, respectively. An antibody or other compound (e.g. organic, peptide or polypeptide molecule) can be designed or identified that specifically recognizes and neutralizes the thrombin/thrombomodulin complex and not free thrombin. Based upon known inhibitors for thrombin itself, which will have a different affinity for the thrombin/thrombomodulin complex, such a molecule can be a small organic molecule, similar to argatroban, a thrombin inhibitor; a small protein, like hirudin, another thrombin inhibitor; or a larger protein, like antithrombin III.

"Antibodies (Abs)" are glycoproteins exhibiting binding specificity to a specific antigen (i.e. thrombomodulin or thrombin).

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains ($C_H$). Each light chain has a variable domain at one end ($V_L$) and a constant domain at its other end; the constant domain of the light chain is aligned with the first constant domain of the heavy chain.

and the light chain variable domain is aligned with the variable domain of the heavy chain. Particular amino acid residues are believed to form an interface between the light and heavy chain variable domains (Clothia et al., *J. Mol. Biol.* 186, 651–663 [1985]; Novotny and Haber, *Proc. Natl. Acad. Sci. USA* 82, 4592–4596 [1985]).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E. A. et al., *Sequences of Proteins of Immunological Interest* National Institute of Health, Bethesda, Md. [1991]). The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$–$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The light chains of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immonoglobulins: IgA, IgD, IgE, IgG and IgM, and several of these may be further divided into subclasses (isotypes), e. g. IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "antibody" is used herein in the broadest sense and specifically covers single monoclonal antibodies antibody compositions with polyepitopic specificity, as well as antibody fragments (e.g., Fab, F(ab')$_2$, and Fv) so long as they exhibit the desired biological properties.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Köhler & Milstein, *Nature* 256:495 (1975), or may be made by recombinant DNA methods [see, e.g. U.S. Pat. No. 4,816,567 (Cabilly et al.)].

The monoclonal antibodies herein, specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.; Morrison et al., *Proc. Nat. Acad. Sci. USA* 81, 6851–6855 [1984]).

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. (For further details see: Jones et al., *Nature* 321, 522–525 [1986]; Reichmann et al., *Nature* 332, 323–329 [1988]; and Presta, *Curr. Op. Struct. Biol.* 2 593–596 [1992]).

"Cytokine" is a generic term for proteins released by one cell population which act on another cell as intercellular mediators. Included among the cytokines are native tumor necrosis factor-α and -β (TNF-α and -β), interferons (IFNs) such as, IFN-α, IFN-β and IFN-γ, interleukins (ILs) such as, IL-1, IL-2, IL-3, IL-4, IL-5, IL-6, IL-7, IL-8, etc., growth hormones (GHs), including human growth hormone (hGH), N-methionyl hGH; and bovine GH; insulin-like growth factors, parathyroid hormone, thyroxine, insulin, proinsulin, relaxin, prorelaxin, glycoprotein hormones such as, follicle stimulating hormone (FSH), thyroid stimulating hormone (TSH), and luteinizing hormone (LH), hemopoietic growth factor, HGF, fibroblast growth factor, prolactin, placental lactogen, mullerian inhibiting substance, mouse gonadotropin-associated peptide, inhibin, activin, vascular endothelial growth factor, integrin, thrombopoietin, nerve growth factors, such as NGF-β, PDGF, transforming growth factors (TGFs) such as, TGF-α and TGF-β, insulin-like growth factor-1 and -2 (IGF-1 and IGF-2), erythropoietin, osteoinductive factors, colony stimulatina factors (CSFS) such as, M-CSF, GM-CSF, and G-CSF, and other polypeptide factors of any human and non-human animal species, and functional derivatives of such native proteins. The cytokines useful in the compositions and methods of the present invention are characterized by exhibiting one or more of the following properties stimulation of procoagulant activity, stimulation of natural killer (NK) and lymphokine-activated killer cell-mediated cytotoxicity, macrophage activation, stimulation of Fc receptor expression on mononuclear cells and antibody-dependent cellular cytotoxicity (ADCC), and enhancement of HLA class II antigen expression. Preferably, the cytokines to be used in accordance with the present invention should have the ability to stimulate procoagulant activity. Particularly referred cytokines are native TNF-α and -β, interleukin-1 and -2, interferon-γ, alone or in combination, and functional derivatives of these native proteins.

The amino acid and nucleotide sequences of human and various animal TNFs-α are well known in the art. TNF-α was described by Pennica et al., *Nature* 312, 721 (1984); TNF-β (LT) was described by Gray et al., *Nature* 312, 724 (1984). The term "TNF-α" as used throughout the specification and claims refers to a native tumor necrosis factor-α (native TNF-α) and its functional derivatives. The phrases "native tumor necrosis factor-α" and "native TNF-α", which are used Interchangeably, refer to a TNF-α polypeptide of any human or non-human animal species as occurring in nature. The phrase "native human TNF-α" as used herein refers to a human polypeptide having the amino acid sequence disclosed in U.S. Pat. Nos. 4,879,226 issued 7 Nov. 1989, and 5,288,852 issued 22 Feb. 1994, with or without the initiating methionine and with or without a signal sequence attached to the N-terminus, whether purified from native source, synthesized, produced by recombinant DNA technology or by any combination of these or other methods.

The phrases "tumor necrosis factor-β", "TNF-β", "lymphotoxin" and "LT" are used interchangeably; and refer to a native tumor necrosis factor-β (TNF-β) and its functional derivatives. The phrase "native TNF-β" designates a polypeptide of any human or non-human animal species as occurring in nature. "Native human TNF-β", "native human lymphotoxin" or "native human LT" is a human polypeptide as disclosed in U.S. Pat. No. 4,920,196 issued 24 Apr. 1990, with or without the initiating methionine, with or without a signal sequence attached to the N-terminus, and with or without associated glycosylation, whether purified from native source, synthesized, produced by recombinant DNA technology or by any combination of these and other methods.

In the context of the present invention, the terms "gamma interferon", "interferon gamma", and "IFN-γ" are used interchangeably, and refer to a native IFN-γ and its functional derivatives. The phrase "native IFN-γ" is used to refer to IFN-γ of any human or non-human animal species as occurring in nature. The phrases "native human gamma interferon", "native human interferon gamma" and "native human IFN-γ" refer to a polypeptide having the amino acid sequence disclosed in Gray et al., *Nature* 295, 503–508 (1982), and in U.S. Pat. Nos. 4,762,791, 4,929,544, 4,727, 138 and 4,925,793, irrespective of its way of preparation. The recombinant human IFN-γ of Gray and Goeddel as produced in *E. coli*, consisted of 146 amino acids, the N-terminal position of the molecule commencing with the sequence CysTyrCys. It has later been found that the native human IFN-γ (i.e., that arising from mitogen induction of human peripheral blood lymphocytes and subsequent purification) is a polypeptide which lacks the CysTyrCys N-terminus assigned by Gray et al., supra. More recently, the crystal structure of *E. coli* derived recombinant human IFN-γ (rhIFN-γ) was determined [Ealick et al., *Science* 252, 698–702 (1991)] showing that the protein exists as a tightly intertwined non-covalent homodimer, in which the two identical polypeptide chains are oriented in an antiparallel manner.

In the context of the present invention, the phrases "interleukin-1" and "IL-1" are used interchangeably, and collectively refer to native IL-1 polypeptide hormones, including native interleukin-1α (IL-1α) and native interleukin-1β (IL-1β), and their functional derivatives. The phrase "native IL-1" is used to refer to IL-1 of any human or non-human animal species as occurring in nature. The phrase "native human IL-1" refers to native IL-1α and native IL-1β of human origin as described in U.S. Pat. Nos. 4,894,333 and 4,879,374) irrespective of their way of preparation. The IL-1α and IL-1β proteins were originally both classified as IL-1, based on a shared lymphocyte activation factor activity and their common occurrence in activated macrophages. Although it is now known that their structures are only distantly related, they are both included in the term "IL-1" in view of their shared biological activities.

The phrase "inducer of cytokine production" as used herein refers to any compound or intervention that results in the induction of in vivo cytokine production in the patient treated. It is preferred to induce the production of a cytokine which has one or more of the following properties: stimulation of procoagulant activity, stimulation of natural killer (NK) and lymphokine-activated killer cell-mediated cytotoxicity, macrophage activation, stimulation of Fc receptor expression on mononuclear cells and antibody-dependent cellular cytotoxicity (ADCC), and enhancement of HLA class II antigen expression. Preferably, the cytokine induced has the ability to stimulate procoagulant activity. Particularly preferred cytokines are TNF-α and -β, interleukin-1 and -2, interferon-γ, most preferably TNF-β.

A "functional derivative" of a native polypeptide is a compound having a qualitative biological activity in common with the native polypeptide. For example, a functional derivative of a native TNF-α or TNF-β polypeptide is a compound that has a qualitative biological activity in common with a native TNF-α and TNF-β polypeptide, respectively. "Functional derivatives" include, but are not limited to, fragments of native polypedtides from any animal species (including humans), and derivatives of native (human and non-human) polypeptides and their fragments, provided that they have a biological activity in common with a respective native polypeptide. "Fragments" comprise regions within the sequence of a mature native polypeptide. The term "derivative" is used to define amino acid sequence and glycosylation variants, and covalent modifications of a native polypeptide, whereas the term "variant" refers to amino acid sequence and glycosylation variants within this definition. Preferable, the functional derivatives are polypeptides which have at least about 65% amino acid sequence identity, more preferably about 75% amino acid sequence identity, even more preferably at least about 85% amino acid sequence identity, most preferably at least about 95% amino acid sequence identity with the sequence of a corresponding native polypeptide. Amino acid sequence variants of TNF-α that only bind one of the two known native TNF receptors, and are, therefore, expected to be less toxic than the corresponding native TNF-αs are specifically within the definition of TNF-α functional derivatives. Such variants having an amino acid alteration at position 86 are described in EP 563,714.

Identity or homology with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as tart of the sequence identity Neither N- or C-terminal extensions nor insertions shall be construed as reducing identify or homology.

"Biological activity" in the context of the definition of functional derivatives of the native cytokines to be administered in accordance with the present invention is defined as the possession of at least one of the following properties: stimulation of procoagulant activity, stimulation of natural killer (NK) and lymphokine-activated killer cell-mediated cytotoxicity macrophage activation, stimulation of Fc receptor expression on mononuclear cells and antibody-dependent cellular cytotoxicity (ADCC); and enhancement of HLA class II antigen expression. The biological activity of cytokines is usually tested in well established cell assays of cytotoxicity such as, for examples in assays based on killing of L929 cells or derivative cell lines.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids
 Acidic Residues: aspartic acid, glutamic acid
 Basic Residues: lysine, arginine, histidine II. Uncharged Amino Acids
 Hydrophilic Residues: serine threonine asparagine, glutamine
 Aliphatic Residues: glycine, alanine, valine, leucine, isoleucine
 Non-polar Residues: cysteine, methionine, proline
 Aromatic Residues: phenylalanine, tyrosine, tryptophan The term "amino acid sequence variant" refers to molecules with some differences in their amino acid sequences as compared to a corresponding native polypeptide or a fragment thereof. Ordinarily, the amino acid sequence variants will possess at least about 65%, preferably at least about 75%, more preferably at least about 85%, most preferably at least about 95% homology with the amino acid sequence of a native polypeptide or, alternatively, are encoded by DNA capable, under stringent conditions, of hybridizing to the complement of the corresponding native polypeptide.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

The term "glycosylation variant" is used to refer to a molecule having a glycosylation profile different from that of a corresponding native polypeptide. Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamlno acid, most commonly serine or threonine, although 5-hydroxyproline or 5-hydroxylysine may also be involved in O-linked glycosylation. Any difference in the location and/or nature of the carbohydrate moieties present in a variant or fragment as compared to its native counterpart is within the scope herein.

The glycosylation pattern of native polypeptides can be determined by well known techniques of analytical chemistry, including HPAE chromatography [Hardy, M. R. et al., *Anal. Biochem.* 170, 54–62 (1988)], methylation analysis to determine glycosyl-linkage composition [Lindberg, B., *Meth. Enzymol.* 28, 178–195 (1972); Waeghe, T. J. et al., *Carbohydr. Res.* 123, 281–304 (1983)], NMR spectroscopy, mass spectrometry, etc.

"Covalent derivatives" include modifications of a native polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected side-chains or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the functional derivatives of native cytokine polypeptides as defined in the present invention. Other post-translational modifications include hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

The phrase "therapeutically effective amount of a combination of a thrombomodulin inhibitor and a cytokine or an inducer of cytokine production (cytokine inducer)" is used herein to refer to a dosage in which the thrombomodulin inhibitor and the cytokine or cytokine inducer in combination cause hemorrhagic necrosis of a tumor. "Effective" treatment preferably results in a visible tumor regression, and in improvement in the quality or life of the patient. Most preferably, the treatment results in an increase in the life span of the patient treated.

The term "combination" in the foregoing phrase means the combined application of a thrombomodulin inhibitor and a cytokine or an inducer of cytokine production, either simultaneously or consecutively, in either order. If the thrombomodulin inhibitor and cytokine or cytokine inducer are administered consecutively, the administration should take place at times sufficiently close to permit that the components exert their respective biological activities in an overlapping time frame. Thus, the term "combination" as used above specifically includes the administration of a thrombomodulin inhibitor and a cytokine or an inducer of cytokine production consecutively, several hours (e.g. 3–4 hours) apart, in either order.

B. Detailed Description of Preferred Embodiments

In a preferred embodiment, a patient diagnosed with a solid, microvasculated tumor is treated with an active-site blocked thrombin and a cytokine, e.g. lymphotoxin (LT)

Thrombin can be prepared from prothrombin by a variety of procedures, such as those described by Miletich, J. et al., *J. Biol. Chem.* 253, 6908 (1978); Morita, T. et al., *J. Biochem.* 79, 1091 (1986): Franza, R. B. et al., *J. Biol. Chem.* 250, 7057–7068 (1975); Fenton, J. W. et al., *Biochim. Biophys. Acta* 229, 26 (1971).

Thrombin is a member of the well characterized family of serine proteases. These proteins catalyze the cleavage of peptide bonds in other proteins, and have a common three-dimensional structure. The location and function of the essential amino acids for activation and catalysis have been identified (Stroud, R. M. et al., *Ann. Rev. Biophys. Bioeng.* 6, 177 [1977]; Bode, W. et al., *J. Mol. Biol.* 118, 99 [1978]; Kraut J., *Annu. Rev. Biophys. Eng.* 6, 177 [1982]). All members of the family have a conserved catalytic mechanism, with the critical active site residues consisting of His$^{57}$, Asp$^{102}$, and Ser$^{195}$, where the numbering, according to accepted convention, is based on the amino acid numbering of chymotrypsin. The specificity for the residue to be cleaved is provided by the residue at position 189. In the case of the blood coagulation proteases, the residue at position 189 is an aspartic acid, resulting in the specificity of these proteases for cleavage at arginine or lysine residues.

The thrombin utilized in the experimental work underlying the present invention was inactivated by means of an active site-specific reagent, D-PheProArg chloromethyl ketone (PPACK) as described in Example 1. However, other reagents, such as other tripeptide chloromethyl ketones, e.g. D-TyrProArg chloromethyl ketone (YPACK, Bachem Bioscience, Inc., Philadelphia), and the thrombin active site inhibitors disclosed in EP 589,741 are also suitable. In general, inactivation can be achieved by any reagent that covalently reacts with an active site residue of thrombin, such as PPACK, YPACK, diisopropylfluorophosphate, p-toluenesulfonylsinechloromethyl ketone, etc., or is capable of non-covalent, high affinity association with the active site of thrombin, provided that the resultant thrombin still maintains the ability to bind to thrombomodulin.

Figure 2A:
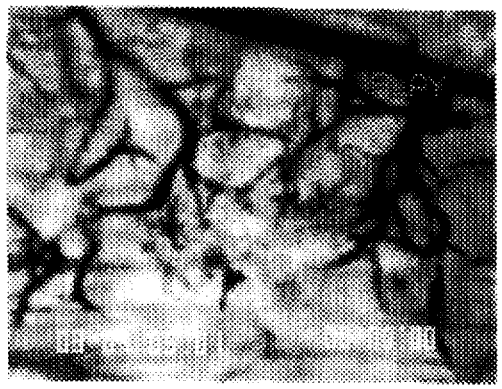
FIGS. 2A–D shows the response of solid mouse tumors to treatment with active site-blocked thrombin and TNF-β. The vessels of the normal subcutaneous skin tissue as well as of transplanted tumors was monitored continuously using an inverted microscope.
Figure 2B:
Figure 2C:
Figure 2D:

Alternatively, a catalytically inactive thrombin variant can be generated by techniques of recombinant DNA technology, e.g. by site-specific mutagenesis of DNA that encodes native thrombin or an earlier prepared thrombin variant. This can be achieved, for example, by altering any of the active site residues (His$^{57}$, Asp$^{102}$, and/or Ser$^{195}$) to amino acid(s) not capable of facilitating catalysis. Alternatively, the binding pocket can be modified changing Asp$^{189}$ to Glu or a similar residue can result in a molecule incapable of cleaving at Arg or Lys residues (therefore incapable of activating protein C), while retaining the ability to bind thrombomodulin. Additional residues that should interfere with substrate cleavage, while not affecting throinbomodulin binding, can be identified from the review by Bode and Stubbs, supra, FIG. 2. Such mutations (amino acid substitutions)., alone or in combination, are also within the scope of the present invention.

Sites or regions that have been identified for substitutions that interfere with the catalytic function of thrombin without affecting its ability of binding thrombomodulin are then usually modified in series e.g. by (1) substituting first with conservative choices and then with more radical selections depending upon the results achieved, (2) deleting the target residue or residues, or (3) inserting residues of the same or different class adjacent to the located site, or combinations of options 1–3.

One helpful technique is called "alanine scanning" (Cunningham and Wells, *Science* 244, 1081–1085 [1989]). Here, a residue or group of target residues is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding a desired variant can be obtained by chemical syntheses using one of the methods described in Engels and Uhlmann, *Agnew. Chem. Int. Ed. Engl.* 28, 716 (1989). These methods include triester, phosphite, phosphoramidite and H-phosphonate methods, PCR and other autoprimer methods, and oliaonucleotide syntheses on solid supports.

More preferably, DNA encodina a desired, active-site blocked amino acid sequence variant of thrombin is prepared by site-directed mutagenesis of DNA that encodes an earlier prepared variant or a nonvariant version or the thrombin molecule. Site-directed (site-specific) mutagenesis allows the production of thrombin variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al., *Meth. Enzymol.* 153, 3 [1987]) may be employed to obtain single-stranded DNA. Alternatively; nucleotide substitutions are introduced by synthesizing the appropriate DNA fragment in vitro, and amplifying it by PCR procedures known in the art.

In general site-specific mutagenesis herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate host cells such as JP101 cells, and clones are selected that include recombinant vectors bearing the mutated sequence arrangement. Thereafter; the mutated region may be removed and placed in an appropriate expression vector for protein production.

The PCR technique may also be used in creating amino acid sequence variants of a thrombin molecule. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp$^R$ kits (obtained from Perkin-Elmer Cetus, Norwalk, Conn. and Emeryville, Calif., and 25 pmole of each oligonucleotide primer, to a final volume of 50 μl. The reaction mixture is overlayered with 35 μl mineral oil. The reaction is denatured for 5 minutes at 100° C., placed briefly on ice, and then 1 μl *Thermus aquaticus (Taq)* DNA polymerase (5 units/1), purchased from Perkin-Elmer Cetus, Norwalk, Conn. and Emeryville, Calif.) is added below the mineral oil layer The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50% vol), and ethanol precipitated, and the DNA is recovered by standard procedures. This material is subsequently subjected to appropriate treatments for insertion into a vector.

Another method for preparing active-site blocked substitution variants of thrombin, cassette mutagenesis, is based on the technique described by Wells et al. [*Gene* 34, 315 (1985)]. The starting material is the plasmid (or vector) comprising the thrombin DNA to be mutated. The codon(s) to be mutated within the thrombin molecule are identified. There must be a unique restriction endonuclease site on each side of the identified mutation site(s). If no such restriction sites exist, they may be generated using the above-described oligonucleotide-mediated mutagenesis method to introduce them at appropriate locations in the thrombin DNA. After the restriction sites have been introduced into the plasmid, the plasmid is cut at these sites to linearize it A double-stranded oligonucleotide encoding the sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated thrombin DNA sequence.

Additionally, the so-called phagemid display method may be useful in making amino acid sequence variants of native or variant thrombin molecules. This method involves (a) constructing a replicable expression vector comprising a first gene encoding the thrombin to be mutated, a second gene encoding at least a portion of a natural or wild-type phage coat protein wherein the first and second genes are heterologous, and a transcription regulatory element operably linked to the first and second genes, thereby forming a gene fusion encoding a fusion proteins (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element; and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli.*

Further details of the foregoing and similar mutagenesis techniques are found in general textbooks; such as, for example, Sambrook et al., *Molecular Cloninig: A Laboratory Manual*, second edition, Cold Spring Harbor Laboratory Press, New York, 1989, and *Current Protocols in Molecular Biology*, Ausubel et al. eds., Greene Publishing Associates and Wiley-Interscience, New York, 1991.

Alternatively, the catalytically inactive thrombin variants which retain the ability to bind thrombomodulin can be prepared by deletion of one or more of the catalytic site residues or other residues or regions that were identified for alterations by one or more of the foregoing techniques. Deletional variants of native thrombin can be prepared essentially following the site-specific mutagenesis techniques described hereinabove for making amino acid substitutions in the thrombin molecule. In addition, restriction endonuclease digestion of DNA followed by ligation may be used to generate active-site deleted thrombin variants, as described in section 15.3 of Sambrook et al., supra. To use this method, it is preferable that the foreign DNA be inserted into a plasmid vector. A restriction map of both the inserted DNA and the vector must be known. The inserted DNA must have unique restriction sites that are not present in the vector. Deletions are then made in the inserted DNA by digesting it between these unique restriction sites, using the appropriate restriction endonucleases under conditions suggested by the manufacturer of the enzymes. If the restriction enzymes create blunt ends or compatible ends, the ends can be directly ligated together using a ligase such as bacteriophage T4 DNA ligase and incubating the mixture at 16° C. for 1–4 hours in the presence of ATP and ligase buffer as described in section 1.68 of Sambrook et al., supra. If the ends are not compatible, they must first be made blunt using the Klenow fragment of DNA polymerase I or bacteriophage T4 DNA polymerase both of which require the four deoxyribonucleotide triphosphate to fill-in the overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase. The resulting molecule is an active-site deleted variant of thrombin.

Amino acid insertions may also yield thrombin variants that are no longer catalytically active but are able to bind thrombomodulin. To construct insertion variants, a strategy similar to the construction of deletion variants may be used, as described in section 15.3 of Sambrook et al., supra. After digestion of the DNA inserted into the plasmid vector (foreign DNA) at the unique restriction site(s), an oligonucleotide is ligated into the site where the foreign DNA has been cut. The oligonucleotide is designed to code for the desired amino acids to be inserted and additionally has 5' and 3' ends that are compatible with the ends of the foreign DNA that have been digested, such that direct ligation is possible. More preferably, insertional variants of thrombin are made by site-specific mutagenesis of DNA encoding a native thrombin or a thrombin variant, essentially as hereinabove described for the preparation of substitution variants.

Once the nucleic acid encoding an active-site blocked or deleted thrombin variant is available; it is generally ligated into a replicable expression vector for further cloning (amplification of the DNA), or for expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence. Cloning and expression vectors and their components are commercially available, and are disclosed in numerous publications, such as, for example, in U.S. Pat. Nos. 5,190,756 (issued 2 Mar. 1993); 5,156,969 (issued 20 Oct. 1992); 5,270,198 (issued 14 Dec. 1993). Also known are prokaryotic and eukaryotic host cells (including microbes and multicellular organisms) and cloning methodologies suitable for the recombinant production of active-site blocked thrombin variants (see, e.g. the foregoing U.S. Patents; Sambrook et al., supra; and Ausubel et al., eds., supra).

If the thrombomodulin inhibitor is an antibody capable of specific binding to the thrombin binding site(s) of throinbomodulin, or an anti-thrombin antibody capable of selective binding to the thrombomodulin-binding site(s) of thrombin, but without inactivating thrombin, or an antibody that specifically recognizes and neutralizes the thrombin-thrombomodulin complex but not the free thrombin, it can be prepared by methods well known in the art.

Polyclonal antibodies generally are raised in animals by multiple subcutaneous (sc) or intraperitoneal (ip) infections of the antigen (e.g. thrombin or thrombin/thrombomodulin complex) and an adjuvant. It may be useful to conjugate the antigen or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg of 1 µg of conjugate (for rabbits or mice, respectively) with 3 volumes of Freud's complete adjuvant and injecting the solution intradermally at multiple sites. One month later the animals are boosted with ⅕ to ¹⁄₁₀ the original amount of conjugate in Freud's complete adjuvant by subcutaneous injection at multiple sites. 7 to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are used to enhance the immune response.

Monoclonal antibodies are obtained from a population of substantially homogeneous antibodies; i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-thrombomodulin monoclonal antibodies of the invention may be made using the hybridoma method first described by Kohler & Milstein, Nature 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, Monoclonal Antibodies: Principles and Practice, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, J. Immunol. 133:3001 (1984); Brodeur, et al., Monoclonal Antibody Production Techniques and Applications, pp.51–63 (Marcel Dekker, Inc., New York, 1987)].

Culture medium in which hybridoma cells are growing is assayed for production of monoclonal antibodies directed against the desired antigen (e.g. thrombin). Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, Monoclonal Antibodies: Principles and Practice, pp.59–104 (Academic Press; 1986). Suitable culture media for this purpose include, for example; Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., Proc. Nat. Acad. Sci. 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an antigen the neutralization of which results in thrombomodulin inhibition, and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Any method known in the art for separately conjugating the antibody to the detectable moiety may be employed, including those methods described by Hunter, et al., Nature 144:945 (1962); David et al., Biochemistry 13:1014 (1974); Pain, et al., J. Immunol. Meth. 40:219 (1981); and Nygren, J. Histochem. and Cytochem. 30:407 (1982).

The antibodies of the present invention may be employed in any known assay method, such as competitive binding assays, direct and indirect sandwich assays, and immunoprecipitation assays Zola, Monoclonal Antibodies: A Manual of Techniques, pp.147–158 (CRC Press, Inc., 1987).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature 321, 522–525 (1986); Riechmann et al., Nature 332, 323–327 (1988); Verhoeyen et al., Science 239, 1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed 21 Aug. 192, which is a continuation-in-part of application Ser. No. 07/715,272 filed 14 Jun. 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551–255 (1993); Jakobovits et al., Nature 362, 255–258 (1993).

Bispecific antibodies may also be used as thrombomodulin inhibitors in the methods of the present invention. Bispecific antibodies are monoclonal, preferably human or humanized, antibodies that have binding specificities for at least two different antigens. If in the present case, one of the binding specificities may, for example, be for the thrombin binding site(s) of thrombomodulin, while the other one may be for the thrombin-thrombomodulin complex. Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, Nature 305, 537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., EMBO 10, 3655–3659 (1991). According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed 17 Aug. 1992.

For further details of generating bispecific antibodies see, for example, Suresh et al., *Methods in Enzymolocy* 121, 210 (1986).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S Pat. No. 4,676,980, along with a number of cross-linking techniques.

The preferred cytokines to be administered in accordance with the present invention are TNF-α and -β, IL-1, IFN-γ alone or in any desired combination. These cytokines are commercially available or can be made by purification from native sources, by methods of recombinant DNA technology, by chemical synthesis or by combination of these and/or other known techniques. The same techniques are suitable for making amino acid sequence variants of native cytokines, such as TNF-β, TNF-α, IL-1, IFN-γ, etc. as those described in connection with the preparation of inactive amino acid sequence variants of thrombin. Amino acid sequence variants of naturally occurring or known variant procoagulant peptides or polypeptides can also be made in an analogous manner.

In a preferred embodiment, the procoagulant or thrombomodulin inhibitor and the cytokine or inducer of cytokine production are administered in a single dosage, either systemically or at the site of the tumor. The thrombomodulin inhibitor is preferably administered in an amount equal to or in excess of the molar concentration in the patient's body of the material to be inhibited. For example, if he thrombomodulin inhibitor is an active-site blocked thrombin; it is preferably administered in an amount equal to or in excess of the molar concentration of the thrombomodulin in the patient's plasma. The thrombomodulin concentration in the plasma of a normal human individual typically is about 20 ng/ml while in various disease states it can average up to about 80 ng/ml. Similarly, if the thrombomodulin inhibitor functions by blocking the thrombomodulin-binding site or thrombin, it will be administered in an amount equal to or in excess of the molar concentration of thrombin in the patient's plasma. Usually about two to five fold molar excesses calculated for the protein to be neutralized are preferred.

TNF-α may be administered systemically in a human dosage of approximately five to ten percent of the LD$_{50}$ of 100 μg TNF-α/kg of body weight, or about 5–10 μg TNF-α/kg body weight, although lower or higher doses might also be effective, provided that, at higher doses, the cytotoxicity of TNF-α does not outweigh the benefits of the treatment. TNF-α can be administered into the tumor at a dosage between approximately one microgram and 200 micrograms/m$^2$, preferably less than about 25 micrograms/m$^2$. The typical dosages of TNF-β are similar, although, due to its lower toxicity, the dosage of TNF-β in human therapy can be raised up to about 100 μg/kg, and can typically be between about 50 and 80 μg/kg, such as 60 μg/kg.

Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

The actual therapeutic dose of the procoagulants, thrombomodulin inhibitors and, cytokines administered in accordance with the present invention is a function of a variety of parameters, such as the type of tumor to be treatment, the patient's agent and condition. The determination of the actual dose for each situation is well within the skill or a practicing physician.

As mentioned before, the administration of the procoagulant or and the cytokine or inducer of cytokine production may be simultaneous or consecutive, with either agent being administered first. Similarly, the thrombomodulin inhibitor and the cytokine or cytokine inducer may be administered simultaneously or consecutively, in either order. Each agent can be formulated in the same or two separate pharmaceutical compositions. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administrations or by sustained release systems.

The efficacy of the treatment of the present invention can be monitored by a variety of in vivo test methods.

Animal Models

Animal models where the results are reproducible and could reasonably be extrapolated to the human clinical situation are chosen.

1. Treatment of experimental tumors.

The in vivo efficacy of the treatment of the present invention can be studied against chemically induced tumors in various rodent models. For example, Meth A, CMS4, CMS5, CMS21, and WEHI-164 are chemically induced fibrosarcomas of BALB/c female mice (DeLeo et al., *J. Ex. Med.* 146, 720 [1977]) which provide a highly controllable model system for studying the anti-tumor activities of various agents (Palladino et al., *J. Immunol.* 138, 4023–4032 [1987]). Briefly, tumor cell lines are propagated in vitro in cell culture. Prior to injection to the animals, the cell lines are washed and suspended in buffer, at a cell density of about $10\times10^6$ to $10\times10^7$ cells/ml. The animals are then infected subcutaneously with 100 to 200 µl of the cell suspension, allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., *Br. J. Cancer* 41; suppl. 4, 309 [1980]), and evidence indicates that tumors can be started from injection of even a singe cell and that a very high proportion of infected tumor cells survive. For further information about this tumor model see Zacharski, *Haemostasis* 16, 300–320 [1986]), and Example 1 hereinbelow.

2. Treatment of spontaneous animal tumors.

A suitable target for in vivo clinical studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor.

According to an optimal study design, to test the efficacy of the treatment of the present invention cats are randomized into four groups. Group 1 is treated with a combination of a thrombomodulin inhibitor and a cytokine (or inducer of cytokine production), group 2 is treated with the cytokine alone, group 3 is treated with the thrombomodulin alone, and group 4 is untreated (although the addition of this group might not be practicable due to the limited number of animals available). Prior to entry into the study, each cat undergoes complete clinical examination, biopsy, and is scanned by computed tomography (CT). Cats diagnosed with sublingual oral squamous cell tumors are excluded from the study. The tongue can become paralyzed as a result of such tumor, and even the treatment kills the tumor, the animals my not be able to feed themselves. Each cat is treated three times over a period of 5 days. Photographs of the rumors will be taken daily during the treatment period, and at each subsequent recheck. After treatment, each cat undergoes another CT scan. CT scans and thoracic radiograms are evaluated every 8 weeks thereafter. The data are evaluated for differences in survival, response and toxicity between the two groups. Positive response requires evidence of tumor regression, preferably with improvement of quality of life and/or increased life span.

In addition, the efficacy of the treatment disclosed herein may be tested in other spontaneous animal tumors, such as fibrosarcoma, adenocarcinoma, lymphoma, chrondroma, leiomyosarcoma of dogs, cats, and baboons. Of these mammary adenocarcinoma in dogs and cats is a preferred model as its appearance and behavior are very similar to those in humans. However, the use of this model is limited by the rare occurrence of this type of tumor in animals.

The efficacy of combinations of other procoagulants and cytokines is tested in the same animal models, using analogous trial designs.

Human Clinical Trials

Human clinical trials are preferably conducted with patients diagnosed with cancer of the head or neck. These cancers, which are usually linked to excessive cigarette smoking or alcohol abuse, constitute about 4–5% of all cancers in the United States. In about 95% they are squamous cell or epidermoid carcinomas, which arise from squamous epithelium. Due to the local symptoms, such as pain, hoarseness, difficulty swallowing, etc., such tumors are usually diagnosed at an early stage, and are typically not accompanied by distant metastases. The cancers of head and neck are currently treated by surgery and radiotherapy and/or chemotherapy. The prognosis is rather poor; typically approximately 10% of the patients will survive 5 years or more following surgical therapy, depending on the location of the tumor. Efficacy in human clinical trials will require evidence of tumor regression, preferably with improvement of quality of life and/or increased life span.

The treatment of the present invention may be combined with known tumor therapies, such as radiation therapy, chemotherapy, and immunotoxin therapy, including the administration of immunotoxin directed against the tumor vasculature as described by Burrows and Thorpe, supra. Most preferably, the treatment of the present invention is combined with the administration of a (further) inhibitor of the protein C system which may, for example, be antibodies to protein C or activated protein, C, antibodies to protein S, inactivated protein C and C4b binding protein, as described in U.S. Pat. No. 5,147,638. In addition, steroids or other agents known to reduce or prevent platelet loss may be administered prior to, durina or after treatment.

Further details of the invention will be apparent from the following non-limiting Examples.

EXAMPLE 1

Treatment of Large Solid Tumors in Mice with a Combination of Inactivated Thrombin and TNF-β

Inactivation of Thrombin

PPACK (Syn Organon Chemica Alta, Ltd.) was dissolved in 10 mM HCl to a final concentration of 5 mg PPACK/ml. The thrombin concentration has varied between 1 and 5 mg/ml in different preparations. Both human and bovine thrombins have been used as a reagent. Buffers used for inactivation consisted of either 50 mM HEPES, pH 6.5, containing 0.5M NaCl, or 25 mM Tris, pH 7.5, containing 0.15M NaCl. PPACK was added at a 10-fold molar excess over the thrombin. The solution was gently rotated at room temperature for three to four hours. Residual PPACK was removed by repeated diafiltration using an Amicon stirred cell concentrator for small volumes, in a Centricon 10 microconcentrator. The reagent was made to a final concentration of approximately 10 mg/ml PPACK-thrombin. Care was taken that all buffers and equipment be endotoxin free.

Treatment and Evaluation of Tumor Response

Tumor response was evaluated in the mouse using dorsal skin chambers (Leunig, M. et al., *Cancer Res.* 52, 6553–6560 [1992]; Lehr, H. et al., *Am. J. Pathol.* 143, 1055–1062 [1993]). This procedure allows one to monitor continuously the vessels of both the normal subcutaneous skin tissue and of transplanted tumors.

Briefly, dorsal skinfold chamber was implanted on CD6/F1 mice. Lewis lung cell carcinoma tumor spheroids, about 700 µm in diameter, were transplanted into these chambers 2-3 days after the chambers had been implanted. About a week after transplantation of the tumors, when an extensive vascular network has formed, the mice were placed on the stand of an inverted microscope.

The compounds were administered by tail vein injections, either alone or in combination, in volumes not exceeding 200 microliters. TNF-β (LT) (recombinant product from *E. coli*, Genentech, Inc. South San Francisco, Calif.) was used at a dose of 7 µg/mouse, and active site-blocked thrombin (ABT) was used at a dose of 1 mg/mouse.

Response was continuously monitored for the first hour after injection and then, once every hour for the following 24 hours. Contrast enhancement of while blood cell trafficking was obtained by acridine orange injected i.v. prior to the invention of the test material. The observations were recorded on a VHS video cassette recorder for later off-line analysis.

FIG. 2 shows the results of the administration of a mixture of 7 µg of human TNF-β and 1 mg active site-blocked bovine thrombin at various times following treatment. (Similar results were obtained with active-site blocked human thrombin.) The actual times are shown in the lower left corners of FIGS. 2A-D. FIG. 2A shows the tumor neovasculature before treatment at 10×magnification. As shown in FIG. 2B (10× magnification), 6.5 hours after treatment there was increased edema in the tumor. In addition, at this time the blood flow appeared sluggish on the actual video. The picture of FIG. 2C was taken about 23 hours after treatment, and is shown at 4× magnification. The picture shows the area where the tumor was (dark area), and that the vasculature of the tumor is completely eliminated as well as the neighboring preexisting vessels that are in the area of tumor. The picture of FIG. 2D was taken about 25 minutes before the picture of FIG. 2C at a second tumor site in the same animal, and is shown at 1.6× magnification. At this location the same phenomenon (vasculature collapse, including neighboring vessels) occurred as at the site shown in FIG. 2C. The pictures also show that normal tissue (lower left sections of FIGS. 2C and 2D) is unaffected by the therapy. Indeed, according the observation by video camera the normal tissue retained normal blood flow throughout the entire observation period. Treatment with either TNF-β (tested in 2 animals) or ASBT (tested in 3 animals) alone had no effect on tumor blood flow or edema at any time point.

A second study performed with a 2 mg/mouse dose of human ASBT, combined with TNF-β administered at a dose of 7 µg/mouse under otherwise identical conditions also resulted in collapse of the tumor vasculature.

EXAMPLE 2

Treatment of Cats with Oral Squamous Cell Carcinoma with Active-Site Blocked Thrombin and TNF-β.

Cats with histologically confirmed squamous cell carcinoma (SCC) of the oral cavity are treated with a protocol incorporating active-site blocked thrombin and TNF-β. All animals are staged according to World Health Organization guidelines prior to treatment. The treatment protocol incorporates three treatments over a 5-7 day span of time.

Each cat is admitted to the hospital for placement of a central catheter, preferably in the jugular vein. These indwelling catheters are placed in such a way as to remain patent during the entire treatment period. Supportive care is given to each cat as indicated on an individual basis. The supportive care includes, but is not restricted to, intravenous fluid support, intravenous antibiotics, and enteral support.

Active-site blocked thrombin is prepared as described in Example 1, and is employed in a dose of about 30 mg/kg The TNF-β dose is escalated based on a predetermined escalation scheme of 3, 5 and 10 µg/kg. The TNF-β is diluted with sterile saline and placed in a Buretrol® (Add-On Set, Baxter Healthcare Corporation, Deerfield Illinois, USA) IV administration system. The amount of saline used to dilute the TNF-β is 25-50 ml, depending on the amount of TNF-β being administered. Normal cat plasma (0.5-1 ml) is added to the saline to prevent the adhesion of the TNF-β to the plastic of the intravenous administration set and tubing. The active-site blocked thrombin and TNF-β may be co-administered intravenously or administered consecutively in optional order, although predosing with TNF-β is believed to be preferable for maximal effect.

EXAMPLE 3

Treatment of Large Solid Tumors in Mice with Combinations of Procoagulants and TNF-β

Using the animal model and following the protocol described in Example 1, each of six CD6/F1 mice with implanted Lewis lung cell carcinoma tumor was administered a 5 µg/mouse dose of factor IXa in combination with a 7 µg/mouse dose of recombinant TNF-β (produced in *E. coli* at Genentech, Inc.). Five of the six animals treated showed a complete, selective collapse of the tumor vasculature.

In a similar experiment, five tumor-bearing CD6/F1 mice were treated with a 5 µg/mouse dose of tissue factor in combination with 7 µg/mouse TNF-β. Four animals showed a rapid, selective collapse of the tumor vasculature. The blood flow started to shut down as early as about two hours after administration.

The entire disclosures of all citations cited throughout the specification, and the references cited therein, are hereby expressly incorporated by reference.

Although the foregoing refers to particular preferred embodiments it will be understood that the present invention is not so limited. It will occur to those ordinarily skilled in the art that various modifications may be made to the disclosed embodiments without diverting from the overall concept of the invention. All such modifications are intended to be within the scope of the present invention.

I claim:

1. A method for inducing a selective collapse of the vasculature of a solid tumor in a patient comprising administering to said patient a therapeutically effective dose of a combination of a compound preventing the formation of a functional thrombin-thrombomodulin complex selected from the group consisting of a compound selectively blocking thrombomodulin from binding thrombin, a compound selectively blocking thrombin from binding thrombomodulin and a compound selectively blocking the thrombin-thrombomodulin complex and (b) a cytokine selected from the group consisting of TNF-β (LT), TNF-α, IL-1, and IFN-γ.

2. The method of claim 1 wherein said compound preventing the formation of a functional thrombin/thrombomodulin complex is a catalytically inactive thrombin variant, which retains the ability to bind to thrombomodulin.

3. The method of claim 2 wherein the patient is human.

4. The method of claim 3 wherein said thrombomodulin inhibitor is a human thrombin which has its active-site blocked by a covalent reagent.

5. The method of claim 4 wherein said covalent reagent is a tripeptide chloromethyl ketone.

6. The method of claim 5 wherein said ketone is D-PheProArg chloromethyl ketone.

7. The method of claim 5 wherein said ketone is D-TyrProArg chloromethyl ketone.

8. The method of claim 1 further comprising the administration of an inhibitor of the protein C system which is other than a thrombomodulin inhibitor.

9. The method of claim 8 wherein said inhibitor is an anti-protein C monoclonal antibody.

10. The method of claim 2 wherein the administration is simultaneous.

11. The method of claim 10 wherein said catalytically inactive thrombin variant and said cytokine are administered in a single pharmaceutical formulation.

12. The method of claim 2 wherein the administration is consecutive.

13. The method of claim 12 wherein said catalytically inactive thrombin variant is administered first followed by the administration of said cytokine.

14. The method of claim 12 wherein said cytokine is administered first followed by the administration of said catalytically inactive thrombin variant.

15. The method of claim 13 or claim 14 wherein the time between the two consecutive administrations is about 3 to 8 hours.

16. The method of claim 15 wherein said time is about 3 to 6 hours.

17. A composition for inducing a selective collapse of the vasculature of a solid tumor in a patient, comprising a therapeutically effective amount of a combination of a compound preventing the formation of a functional thrombin-thrombomodulin complex selected from the group consisting of a polypeptide or peptide capable of selective binding to a thrombin-binding site of thrombomodulin, a polypeptide or peptide capable of selective binding to a thrombomodulin-binding site of thrombin without inactivating thrombin, and an organic, polypeptide or peptide molecule specifically recognizing and neutralizing the thrombin-thrombomodulin complex and not free thrombin and (b) a cytokine selected from the group consisting of TNF-$\beta$ (LT), TNF-$\alpha$, IL-1, and IFN-$\gamma$.

18. The composition of claim 17 wherein said compound preventing the formation of a functional thrombin/thrombomodulin complex is a catalytically inactive thrombin variant which retains the ability to bind to thrombomodulin.

* * * * *